United States Patent [19]
Shukla et al.

[11] Patent Number: 5,767,775
[45] Date of Patent: *Jun. 16, 1998

[54] UNANCHORED SENSOR AND LEVEL SENSOR

[76] Inventors: Ashok K. Shukla; Mukta M. Shukla, both of 10024 Century Dr., Ellicott City, Md. 21042

[*] Notice: The term of this patent shall not extend beyond the expiration date of Pat. No. 5,625,344.

[21] Appl. No.: 806,112

[22] Filed: Feb. 25, 1997

Related U.S. Application Data

[63] Continuation-in-part of Ser. No. 201,793, Feb. 25, 1994, Pat. No. 5,625,344.

[51] Int. Cl.$^6$ ............................................. G08B 21/00
[52] U.S. Cl. .................... 340/623; 340/603; 340/618; 340/624; 200/61.45 R; 200/84 R; 200/220; 200/223; 200/230
[58] Field of Search ............................. 340/603, 618, 340/623, 624; 200/61.45 R, 61.52, 84 R, 846, 220, 230, 223

[56] References Cited

U.S. PATENT DOCUMENTS

| | | | |
|---|---|---|---|
| 2,692,652 | 10/1954 | Wilson | 200/220 |
| 3,211,853 | 10/1965 | Le Grudisier | 200/84 R |
| 3,719,936 | 3/1973 | Daniels et al. | 340/539 |
| 4,399,338 | 8/1983 | Jones | 340/625 |
| 4,912,662 | 3/1990 | Butler et al. | 345/625 |
| 4,922,234 | 5/1990 | Murphy | 200/84 R |
| 5,228,204 | 7/1993 | Ryan | 340/623 |
| 5,625,344 | 4/1997 | Shukle et al | 340/623 |
| 5,654,692 | 8/1997 | Baxter, Jr. et al. | 340/623 |

*Primary Examiner*—Edward Lefkowitz

[57] ABSTRACT

A device and method for sensing fluid characteristics, including level, temperature, pH and chemistry, comprises a switch affixed to or embedded in a container of a size, shape and density such that said container floats stably in said liquid until a predetermined level is reached; the container tilts so as to operate the switch when the liquid drops below or increases above a predetermined level. The device may contain additional sensors which measure and report other characteristics of the liquid, such as temperature, pH, viscosity, chemistry or biochemistry.

20 Claims, 8 Drawing Sheets

UNANCHORED SENSOR AND LEVEL SENSOR

RELATED APPLICATION

This application is a continuation-in-part of U.S. patent application, Ser. No. 08/201,793 filed Feb. 25, 1994 U.S. Pat. No. 5,625,344.

FIELD AND BACKGROUND OF THE INVENTION

1. Field of Invention

This invention relates to a device and method for sensing fluid characteristics, including level, temperature, pH and chemistry, and more particularly for sensing when, the level of a fluid in a container has reached a predetermined upper or lower limit or when another characteristic has reached a predetermined level.

2. Background Information

The determination of fluid characteristics can be very useful in many processes. For example, if a fluid level is lower or higher than a predetermined level, then a signal can be generated either warning an operator or automatically taking action such as controlling an intake or discharge pump. This will prevent the container from being empty or from overflowing.

Most commercially available level-sensors are joined with wire to a control unit. This limits the applications. Further they are bulky to be fitted in small mouth bottles.

Infrared sensors, that determine fluid level from outside the container, are limited by the color of the container and do not work with opaque containers. Furthermore, this also requires constant power supply. Considering all the systems available, the invention described here has the following advantages:

Small

Unanchored

No power required if not activated.

Does not depend on the type of container; it can be used with virtually any container.

Autoclaveable

Can be made of solvent inert materials, such as TEFLON™. Besides indicating the levels, the level sensor can incorporate or interact with other sensors to indicate parameters e.g. temperature, pH, etc.

The principal objective of this invention is to provide a simple level sensor which can determine the upper and lower limits of fluid in a container, simultaneously if desired. Furthermore, this sensor can transmit a signal to a receiver to immediately interrupt or stop the process. This will avoid the human control or mistake. Further, this sensor should be able to measure other parameters beside level, as in a reaction chamber or fermentor, and transmit the data to a data processor or control unit. This level sensor should be made of a material like TEFLON™ which is inert to most solvents. This unit can be used in fluids of different densities and viscosities.

SUMMARY OF THE INVENTION

It is an object of the invention to provide a fluid level sensor for sensing whether the level of fluid in a container has reached a predetermined upper or lower limit, and to do so without the need for an electrical or other permanent connection to the container and without limitation on the type of container which may be used.

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which:

1a. for the lower level sensor.

1b. for upper level sensor.

1c. for upper and lower level sensors.

FIGS. 2a,b are side views of the device with weight rings for changing the weight for particular fluid density. Further it shows the weight in the container for the direction of tilting the device.

FIGS. 3 a,b, 4 are an enlarged view of a portion of FIG. 1 comprising the schematic view of the sample circuit diagram, which is embodied in the device.

DESCRIPTION OF THE PREFERRED EMBODIMENT

Figure 1A:
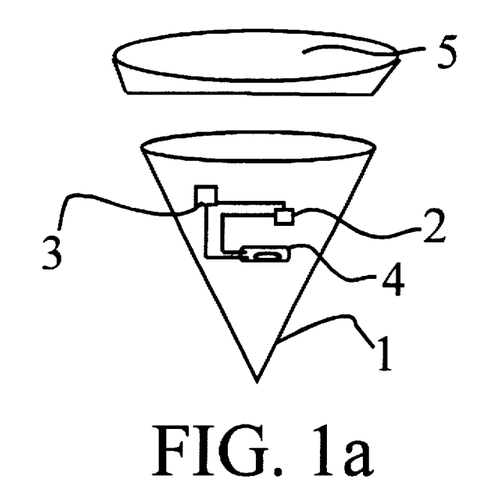
FIG. 1 is an expanded view of one embodiment of a device according to present invention.
Figure 1B:
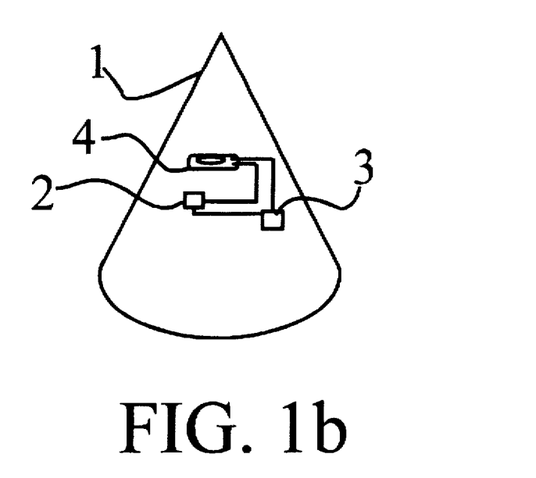
Figure 1C:
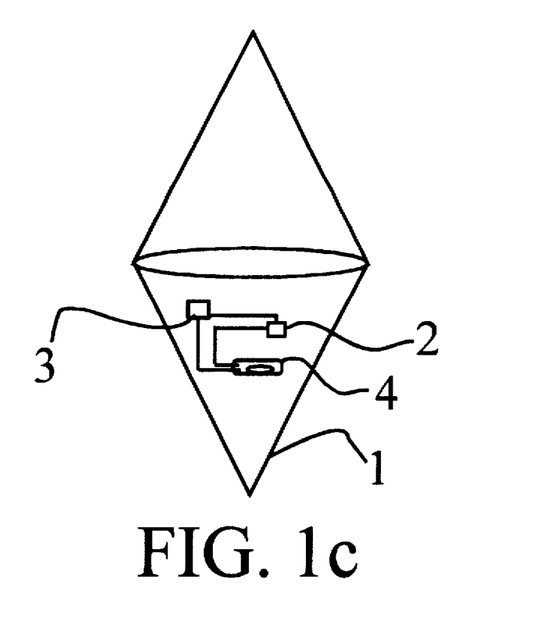

Referring to the drawings, the invention is a levelness sensor (for example, a mercury switch) encapsulated in a conically shaped inert material (such as TEFLON™) (1), sized appropriately to the predetermined fluid limit, and coupled to an alarm device (2), such as an audible alarm, a radio frequency or any other frequency including ultrasound, light emitting diode, infrared diodes and UV-light, powered by a battery (3) in series with either a mercury or any kind of switch (4) and sealed in a capsule or by a cap, (5) shown in overview in FIG. 1. The circuit may contain an inductive coil or frequency transponder with a switch but without a battery (the activation energy for the transponder or inductive coil will be received from a receiver or an outside source), to transmit signals to the receiver.

Figure 2:
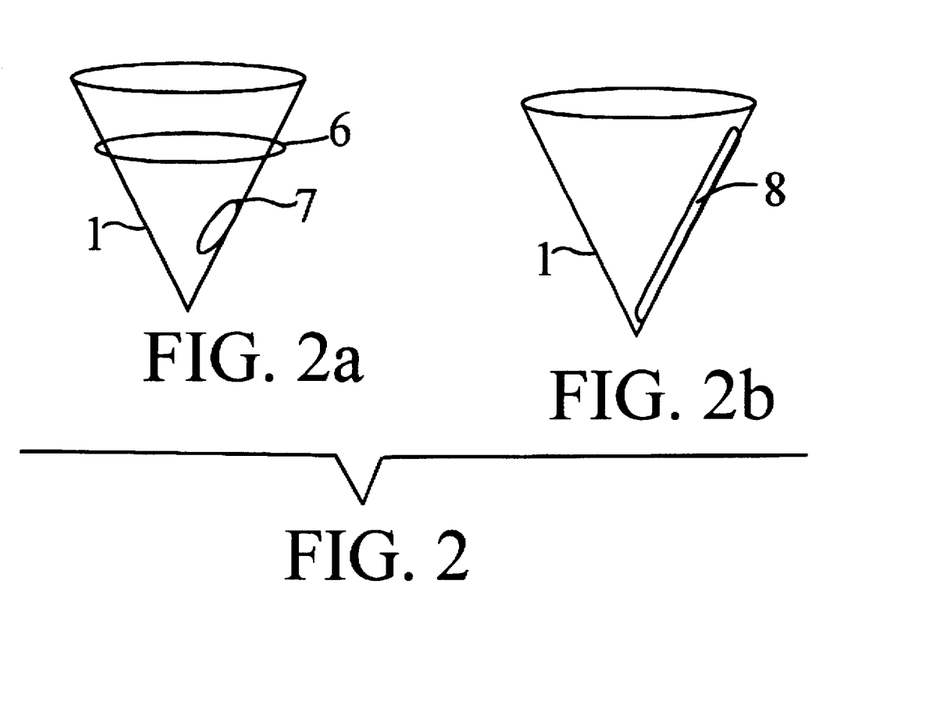
Figure 3:
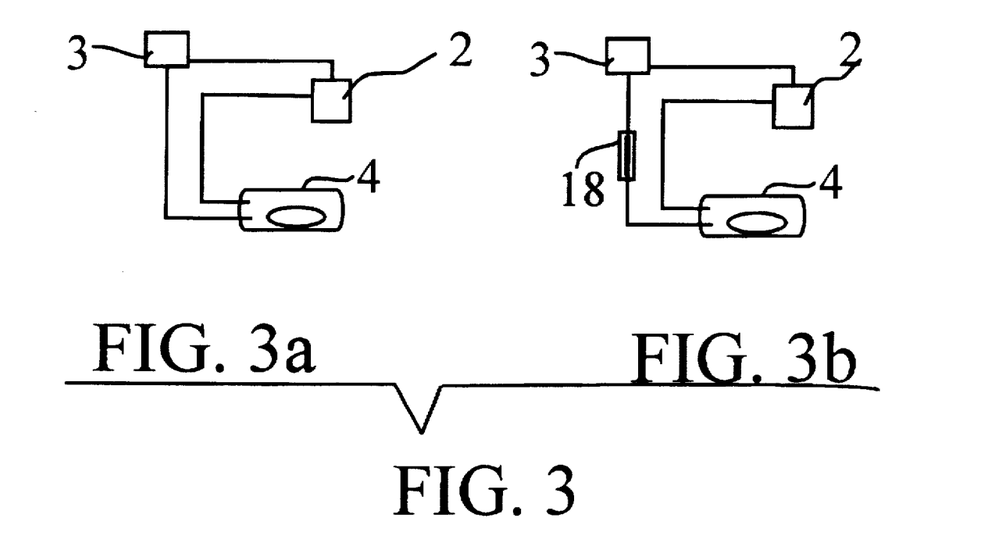
Figure 4:
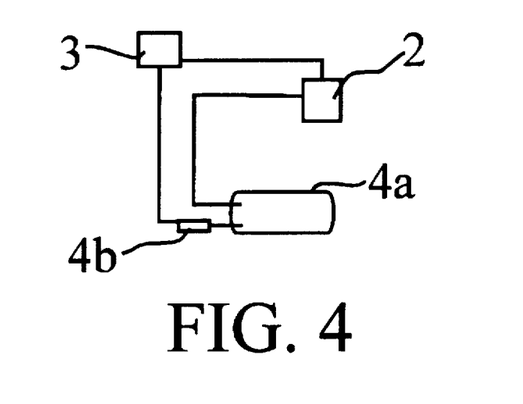

Referring to FIG. 1, the invention is embodied in a monitoring device (1), the preferred embodiment of which is a conical shaped device. In the case of a level sensor, the device may be hollow, but must be of a density that can float on or at a predetermined distance below the liquid surface. As shown in FIG. 2, weight rings (6) are provided if necessary to suit the density of the fluid in which it is to be used. The device (1) can be made of TEFLON™ or any inert material which does not react with the fluid in the container. The device (1) is sealed by cap (5), which can be permanently sealed if desired or molded with electronic in one piece. Furthermore, it may also be designed so as to be resealed for changing the mercury switch (4), the alarm device (2), circuitry or the battery (3) or for adding other elements. Alternative circuits are shown in FIGS. 3 and 4, and in FIG. 4 an inclinometer (4a) coupled to a switch (4b) replaces the mercury switch of FIG. 3. Further in FIG. 3b a switch (18) is built in the device to activate or deactivate the battery during the transport or storage. Further the circuit has the possibility to deactivate after sending the signal and thus save the life of the battery.

Figure 5:
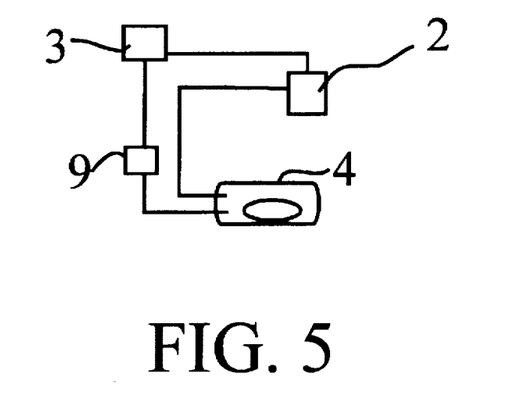
FIG. 5 is an enlarged view of the portion of FIG. 1 comprising the schematic view of the sample circuit diagram with additional sensors.

Furthermore, other sensors (9) can be attached with the same circuit (FIG. 5) or in separate circuits without the level sensor circuit. These sensors could be temperature, pH, enzyme, chemical or biochemical, ion-specific or any other sensor for the process of chemical or biochemical reactions. Furthermore, this kind of device can also be used to measure other characteristics of a liquid e.g. temperature, pH., etc. Where fluid level is not one of the characteristics desired to be measured, the unit need not be conical or a floating device and can just lie at the bottom of the container submerged in the liquid. These sensors can be programmed to be in activation either constantly or only at regular intervals and the activation can be achieved either by sending electronic impulse (radio frequency, etc.) from an external source or mechanically (e.g. stirring).

Figure 6:
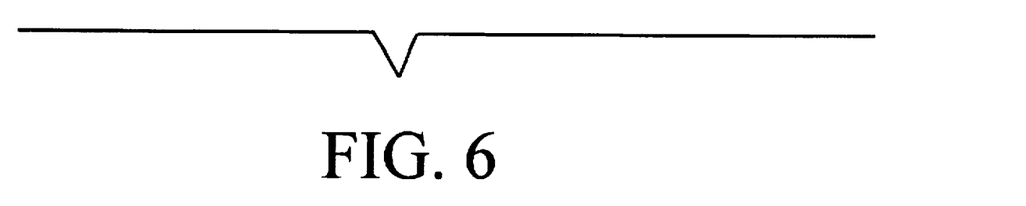
FIGS. 6a, b is a view of portion of FIG. 1 comprising the schematic view of more than one sensor.
FIG. 6b shows a display of parameters determined by the device.
Figures 6A, 6B:
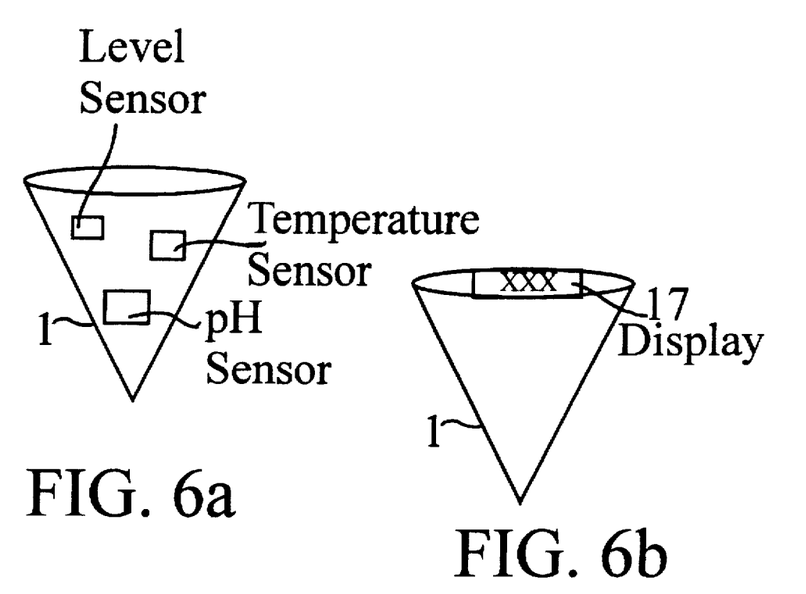
Figures 7, 7C:
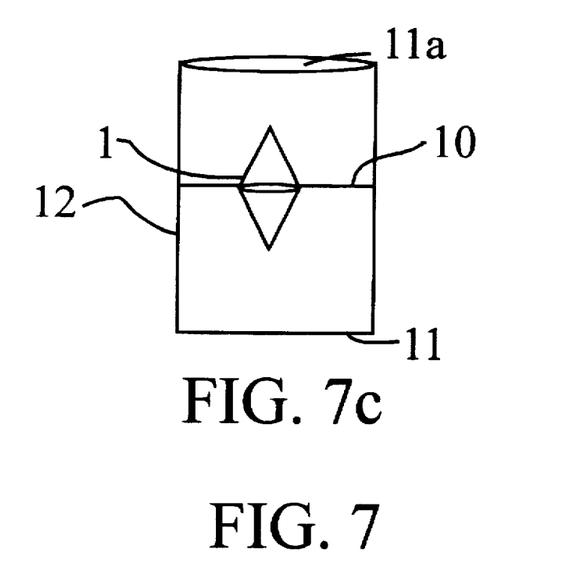
Figure 7A:
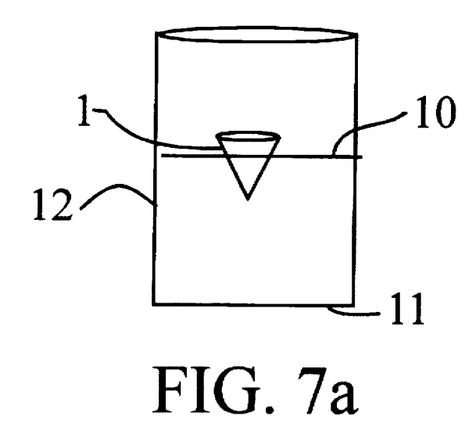
FIGS. 7a, b, c and 8a–d are side views of device in container of fluid illustrating the device in ready mode (7) and in alarm mode (8).
Figure 7B:
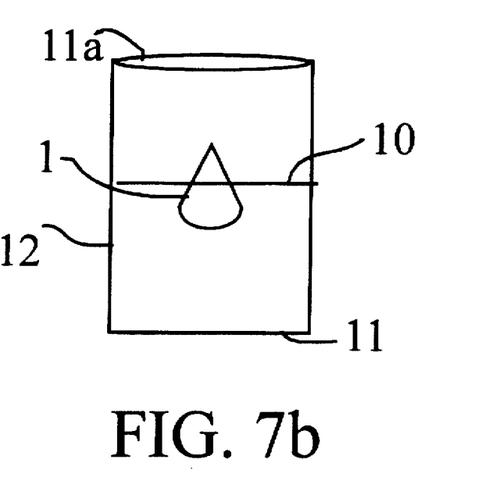

Furthermore, as in FIG. 6b, the device can have one or more displays (17) of the data which can be read directly.

The alarm could be a light source (for example, light emitting, infrared or ultraviolet diode or lamp), sound (beeper)or ultrasound source, or a transmitter (any frequency generator with and/or without a data transmitter).

While the preferred shape is conical where it is desired to sense fluid level, the shape of the device (1) can be other than conical, but if the device is to include a level sensor the geometry should be such that it floats stably in the fluid until the predetermined level has been reached, in order to avoid unintentional activation of the switch. The device should be of such a size and density that it will float until the desired lower or upper level of the fluid is reached, and then will contact the top or bottom of the container, tilt and activate the switch. The tilt angle of a mercury switch could be different for different applications. For example, in case of a boiling liquid, the wave formation of boiling liquid can activate the switch, or as above the switch will activate only if tilted to certain angle.

A conventional mercury switch measures levelness in one direction only. If such a switch is used, it is necessary to assure that the device will tip in the direction necessary to close the switch. As illustrated in FIG. 2, this may be accomplished either by adding a small weight (7) to the device in the direction of desired tilt or making an eccentric cone (8) that will automatically tilt when not floating. The mercury switch is then mounted in the device so as to be level in the operation, accounting for the tilt imparted by the extra weight.

Figure 8A:
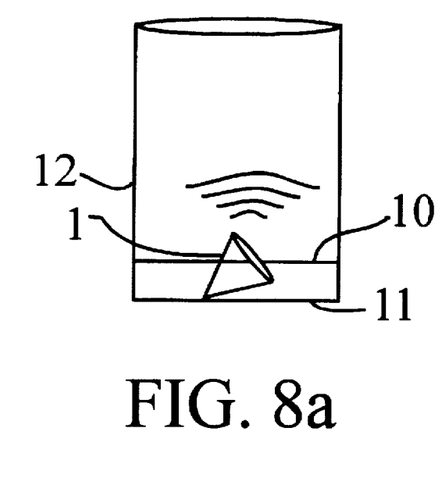
Figure 8B:
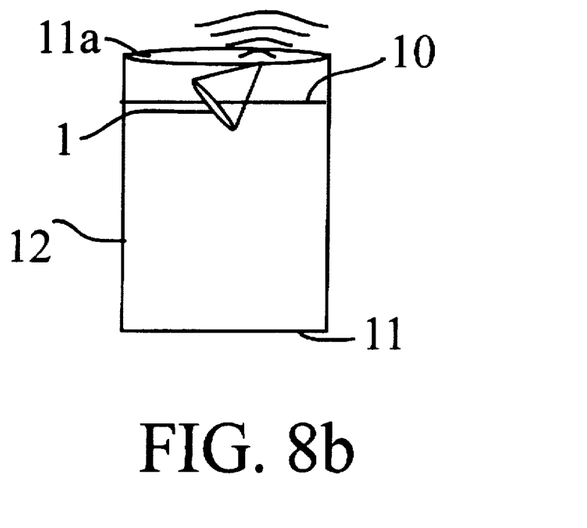
Figure 8C:
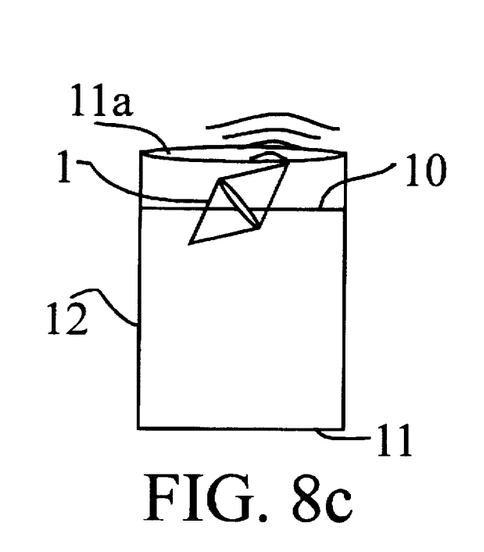
Figure 8D:
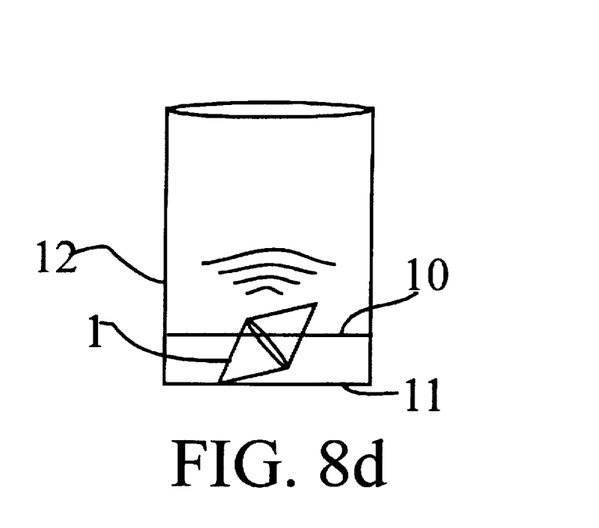
Figure 9A:
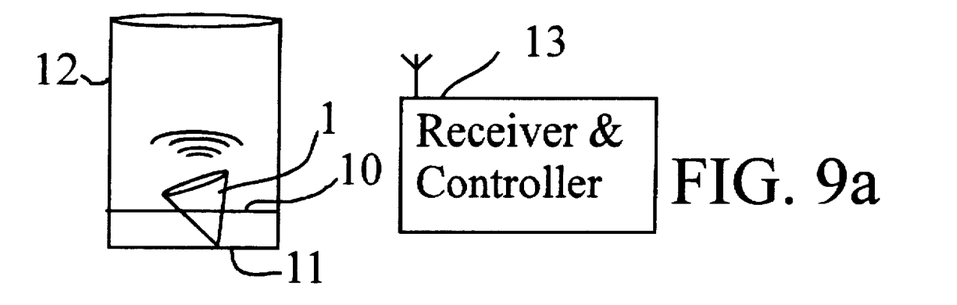
FIGS. 9a, b, c is a schematic illustration of alternative configuration of the device with receiver and control unit.

As shown in FIGS. 8a,b,c when the device (1) floats on the fluid surface (10), it is vertical and the mercury switch will be in the off position, hence there is no current flow. As shown in FIGS. 9a,b,c when the fluid level (10) drops or rises to a certain point which allows to the device (1) to touch the bottom (11) or top (11a) of the container (12), the device will tilt due to its conical shape. As soon as a desired tilt angle (determined by the position of the mercury switch) is achieved, the mercury switch closes the circuit and activates the alarm (for example, light, sound, or a frequency or all together).

Figure 9B:
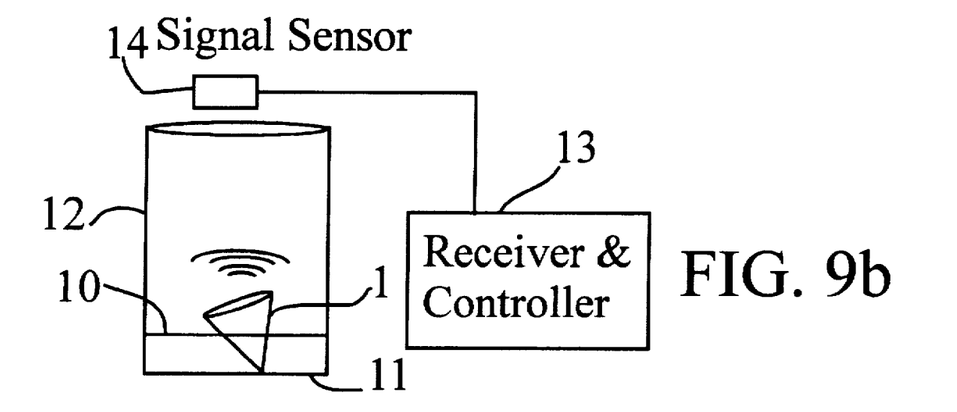
Figure 9C:
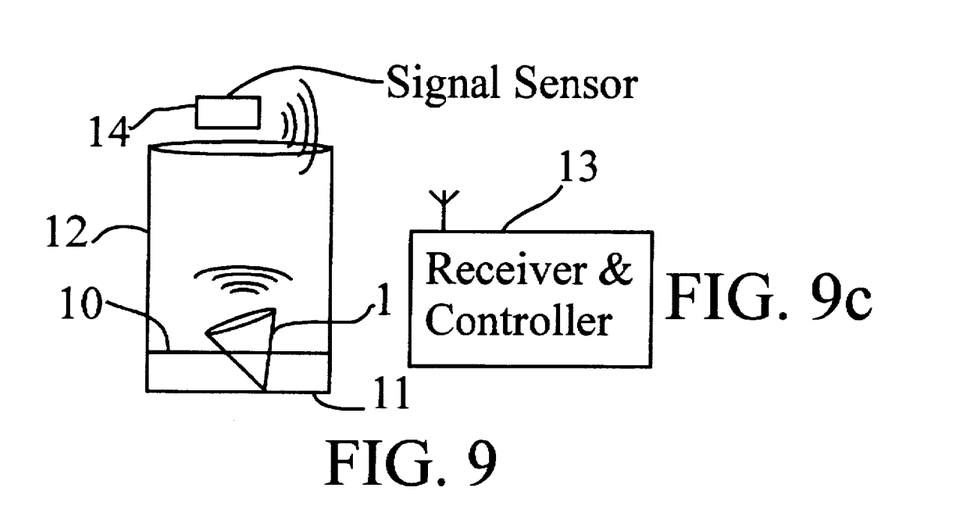

The alarm can be designed to simply alert a human operator of the lower or upper fluid levels, or can be coupled with other devices as in FIG. 9 (for example, through receiver (13) directly or through a sensor (14, FIG. 9b) to take remedial action (for example, shutting off a pump or a heat source), or can be coupled to a timer so as to take automatic remedial action if human operator does not intervene within a predetermined period. If the signals from the device (1) are weak, they can be further amplified by another external device which can be remotely controlled or connected by a wire (14 in FIGS. 9b,c) before being sent to a receiver or a controlling device. This is useful in case of metallic or opaque containers or the device being far away from the receiver.

Figure 10:
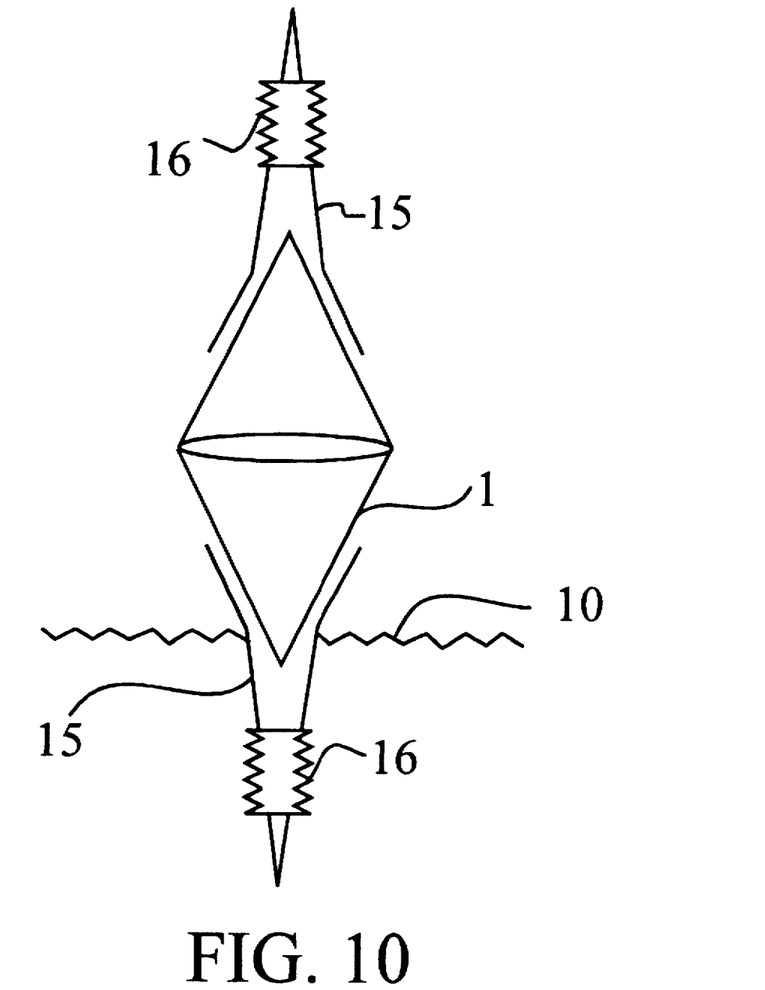
FIG. 10 is a side view of the device attached to a carrier suitable for adjusting the level at which an alarm is triggered.

In addition, as shown in FIG. 10, the device may be attached to a carrier (15) of a suitable size and shape to float when a liquid is above a predetermined level and to contact the container bottom or top, thus tilt, below or above said level. The carrier may be made adjustable by screw (16).

Furthermore as in FIG. 11, more than one device (1) can be placed in this container for upper or lower levels of the fluid and for sending data of some measurements like pH, temp., etc. Therefore, different transmission frequencies can be transmitted by different sensors for different operations. Furthermore, different frequencies can be programmed in different sensors so that many sensors can be operated in the same area.

One or more level sensors can be placed in the same container for the determination of upper and lower limit separately to exclude the error, which could happen due to single unit as it can not differentiate if the mercury switch is activated by upper or lower level in the container.

The mercury switch will be activated by the movement of fluid, for example by fermentation gases, agitation, shaking, or stirring. As soon as liquid does not have any movement it will stop sending the signal.

The broader usefulness of the invention may be illustrated by the following examples.

EXAMPLES OF APPLICATIONS

Example #1

Warning and control of solvent reservoir in Liquid Chromatography

In column chromatography, a solvent flows through a column and various chemicals and biochemicals are separated in the column. The solvent is applied to the column by means of a pump or hydrostatic pressure to maintain a steady solvent flow through system. Column chromatography separation needs to be under constant observation, because if the containers with the solvent run empty then the column runs dry. If the column runs without solvent then it gets dried out due to the air passing through the column. This in turn destroys the column as well as the whole separation process. The column must be replaced and the previously separated substances are lost. Therefore, it is important to monitor the solvent level in the container from time to time and if required to keep refilling the solvent. However, it is most common in the busy daily lab routine and during experiments to sometimes forget refilling. This invention provides a device which can be placed in the solvent container without affecting the operation of the separation process and which can either alert the operator when level is low or can refill and the upper level sensor will shut off the valve once the upper limit is reached.

Example #2
Warning of pre-boiling temperature

An active temperature sensor may be placed in the device (1). The whole unit can be placed in a liquid and temperature sensor adjusted to 5°–10° C. below the boiling point. When the pre-boiling temperature is reached, the device will send a signal warning that boiling is about to occur. This unit can be used in the lab as well as at home for the boiling of fluids, for example milk. The signal can be received by a person or a receiver with a built-in controller to take action (for example shut off the unit). The same unit can be also used as a wireless remote sensing thermometer or thermostat.

Example #3
Remote Controlled pH meter

A pH meter probe can be placed in the device (1). The pH can be measured and the value transmitted to a receiver for control. Such device would be useful in fermentation or other processes.

Example #4
Remote controlled enzyme reactions

Probes such as biosensors of different types, (for example for oxygen, nitrogen, enzyme, alcohol, glucose or substract or products of enzyme reactions) can be included in the device and can be monitored and data can be transmitted directly to control or warning unit. More than one biosensor can be used in a single device and each probe can send a signal to the receiver, which can control and process results simultaneously.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, but is defined by the appended claims.

What is claimed is:

1. An unanchored level sensing device for sensing the level of a liquid in a container and indicating if the level has dropped and/or increased to a predetermined level, comprising a switch affixed to or embedded in a container of a size, shape and density such that said container floats stably in said liquid until said predetermined level is reached, and tilts so as to operate the said switch when said liquid drops below or increases above the said predetermined level.

2. An unanchored level sensing device as in claim 1, wherein said container is conical in shape.

3. An unanchored level sensing device as in claim 1, wherein said switch is a mercury switch embedded in or affixed to said container.

4. An unanchored level sensing device as in claim 1 wherein upper and/or lower level can be adjusted to predetermined levels by an adjustable height rod attached to said device.

5. An unanchored level sensing device as in claim 1 further comprising circuitry for activating an alarm device when said switch is in a predetermined position but not otherwise.

6. An unanchored level sensing device as in claim 5 further comprising an inductive coil or frequency transponder without a battery.

7. An unanchored level sensing device as in claim 5 wherein the said circuit has the possibility to deactivate after sending the signal and thus save the life of the battery.

8. An unanchored level sensing device as in claim 5, wherein said alarm device comprises a frequency generator.

9. An unanchored level sensing device as in claim 8 wherein said frequency generator is a light source.

10. An unanchored level sensing device as in claim 8 wherein said frequency generator is a radio frequency or 900 mega hertz source.

11. An unanchored level sensing device as in claim 8 wherein said light source is an infrared light source.

12. An unanchored level sensing device as in claim 8 wherein said frequency generator is a sound or an ultrasound source.

13. An unanchored level sensing device as in claim 5 further comprising a timer for delaying activation for a predetermined period if time.

14. An unanchored level sensing device as in claim 5 further comprising a control device with built-in alarm signal device.

15. An unanchored level sensing device as in claim 8 further comprising a receiver for receiving signals generated by said frequency generator, said receiver being coupled to a control device for controlling the level of said liquid.

16. An unanchored sensing device as in claim 1 further comprising a sensor for sensing a characteristic of said liquid and a transmitter for transmitting information concerning said characteristic to a receiving device for receiving said information, said receiving device being external to said liquid.

17. An unanchored sensing device as in claim 16 further comprising display means for displaying a visual representation of the characteristic being measured.

18. An unanchored sensing device as in claim 16 wherein said sensor is a pH, temperature, viscosity, enzyme, affinity, ion, conductivity, chemical or biochemical sensor.

19. An unanchored sensing device as in claim 16 or 18, wherein said sensor comprises one or more sensors in the device.

20. An unanchored liquid level sensor device for sensing if liquid levels in a container have dropped or increased to a predetermined level, comprising inclinometer means coupled to a switch such that said switch is open when the inclinometer is level and closed when the inclinometer deviates from level by a predetermined amount, said inclinometer and switch being affixed to a container of such size and density that said container floats stably in said liquid until said predetermined level is reached and tilts so as to cause said inclinometer to close said switch when said liquid drops or raises said predetermined level.

* * * * *